United States Patent
Bergeron et al.

(10) Patent No.: US 6,889,830 B2
(45) Date of Patent: *May 10, 2005

(54) DEVICE FOR SEPARATING THE CONNECTING END OF A HYPODERMIC NEEDLE FROM THE TIP OF AN INJECTION INSTRUMENT

(75) Inventors: Luc Bergeron, Boussens (CH); Grégoire Bosset, Preverenges (CH); Jérôme Moulin, St-Maurice (CH); Laurent Soldini, Lausanne (CH)

(73) Assignee: Ares Trading S.A., Varmarcus (CH)

( * ) Notice: Subject to any disclaimer, the term of this patent is extended or adjusted under 35 U.S.C. 154(b) by 181 days.

This patent is subject to a terminal disclaimer.

(21) Appl. No.: 10/289,856

(22) Filed: Nov. 7, 2002

(65) Prior Publication Data

US 2003/0078543 A1 Apr. 24, 2003

Related U.S. Application Data

(63) Continuation of application No. PCT/IB01/00818, filed on May 14, 2001.

(30) Foreign Application Priority Data

May 15, 2000 (EP) .............................................. 00810416

(51) Int. Cl.$^7$ ........................... B65D 83/10; A61B 5/00; A61M 5/32
(52) U.S. Cl. ....................... 206/365; 206/366; 600/576; 600/577; 604/192
(58) Field of Search .............................. 206/365–366; 220/908; 604/110, 192, 263; 600/576, 577; 29/240

(56) References Cited

U.S. PATENT DOCUMENTS

| 4,932,418 A | * | 6/1990 | Coburn ........................ 600/577 |
| 4,989,307 A | * | 2/1991 | Sharpe et al. .................. 29/240 |
| 5,092,462 A | * | 3/1992 | Sagstetter et al. ........... 206/366 |
| 5,273,161 A | * | 12/1993 | Sagstetter .................... 206/366 |
| 5,409,112 A | * | 4/1995 | Sagstetter .................... 206/366 |
| 5,545,145 A | * | 8/1996 | Clinton et al. ............... 604/192 |
| 5,810,167 A | * | 9/1998 | Fujii ........................... 206/365 |
| 5,873,462 A | | 2/1999 | Nguyen |
| 5,968,021 A | | 10/1999 | Ejlersen |

FOREIGN PATENT DOCUMENTS

| EP | 0 364 839 | 4/1990 |
| WO | WO 92/13585 | 8/1992 |
| WO | WO 97/40869 | 11/1997 |

* cited by examiner

Primary Examiner—Bryon P. Gehman
(74) Attorney, Agent, or Firm—Sturm & Fix LLP

(57) ABSTRACT

The connecting end of the hypodermic needle is so designed that it can be attached to and then disconnected from the tip of an injection instrument by pressure, that is, an axial tractional force exerted between the said needle and the said injection instrument. The extraction device has an opening delimited by locking elements forming one piece with elastic pieces so as to allow its diameter to vary between a minimum diameter and a maximum diameter at least equal to the diameter of the said connecting end and at least one piece associated with the said locking elements for the purpose of converting an axial force exerted on the said piece into at least one radial component capable of being applied to the said elastic pieces so as to deform them radially in order to increase the diameter of the said opening when axial pressure is exerted by the said connecting end.

4 Claims, 4 Drawing Sheets

DEVICE FOR SEPARATING THE CONNECTING END OF A HYPODERMIC NEEDLE FROM THE TIP OF AN INJECTION INSTRUMENT

CROSS REFERENCE TO RELATED APPLICATIONS

This application is a Continuation application of PCT/IB01/00818 filed May 14, 2001, claiming priority of European Application No. 00810416.8 filed May 15, 2000, entitled Device for Separating the Connecting End of a Hypodermic Needle From the Tip of an Injection Instrument, which are included in their entirety by reference made hereto.

TECHNICAL FIELD OF THE INVENTION

The invention relates to a device for separating the connecting end of a hypodermic needle from the tip of an injection instrument, the connecting end of the said needle having connectors complementary to the connectors on the said tip, one of the said connectors having radial elasticity and devices for converting an axial force exerted between the said needle and the said injection instrument into at least one radial component capable of deforming the said elastic connectors.

BACKGROUND OF THE INVENTION

Hypodermic needles of this type are found on the market. Fixing them on the tip of an injection instrument is easier and faster because it is no longer necessary to screw the needle on, simple axial pressure sufficing to make the complementary connectors engage with each other. Theoretically separation by axial traction should also be possible but the lack of purchase makes this operation difficult for most people, and therefore it is effected in the traditional manner by unscrewing.

Given that in the case of chronic disorders requiring the daily injection of medical substances it is frequently the patient who must perform self-injection making it easier to handle injection needles meets a need, especially for the purpose of facilitating their safe removal, disposal or storage.

International publication WO 92/13585 (Aug. 20, 1992) describes a needle container comprising a conical housing. Prior to use, the needle is held by frictional forces at the open end of the conical housing. After use of the needle, the user can re-insert the needle into the conical housing, pushing the needle below elastic tabs at the open end of the conical housing. The resilient tabs snap back after the needle is fully inserted, preventing the needle from being withdrawn.

EP 0 364 839 discloses a syringe for medical use of the disposable type provided with a hollow cap that can be super-imposed to the needle to protect it after carrying out the injection. Close to the opening of the cap cavity, members are provided that firmly engage the collar of the needle when it is forced into the cap cavity.

In all of the prior art cases, when the needle is fixed at the outlet end of the syringe, the user is no longer protected from injury by the needle. Several injection devices have been proposed to obviate this inconvenience and comprise to this end a mechanism for effecting the injection, which is movable by a cocking means counter to the force of a spring into a cocking position, from which it can be released to effect an injection process, so as to act upon a piston containing fluid to be injected.

A device of this type is disclosed for example in EP 0 359 761. The housing of this device is approximately the shape of an oversize fountain pen, and the injection needle is inside the device as long as injection process is not being performed. The injection device has a mechanism used to effect the injection process, which mechanism can be moved by means of a cocking element counter to the force of a spring into a cocked position from which it can be released in order to effect an injection process. This mechanism moves the hypodermic needle axially so that it protrudes from the forward end of the housing of the device which is put into contact with the skin of the patient so that it is inserted through the skin and the liquid is injected.

With such a device, except during the injection process, the needle is inside the cylindrical barrel of the injection device, so that the user cannot see the precise position of the needle to be introduced into the opening of the housing in which the needle has to be separated from the injection device, since it is hidden from sight by the cylindrical barrel of the injection device.

The purpose of the present invention is to make the disposal of the used needles easier.

SUMMARY OF THE INVENTION

To this end the invention refers to a device for separating the connecting end of a hypodermic needle from the tip of an injection instrument, according to claim 1.

The advantage of this device lies in the simplicity both of its design and of its use. The speed of the operation of removing the needle and the possibility of protecting it from any contact after it has been separated from the injection instrument are other advantages of the device.

DETAILED DESCRIPTION OF THE INVENTION

Other advantages and special features of this invention will become apparent from the following description, supported by the attached drawings which illustrate diagrammatically and by way of example various embodiments of the device to which the invention refers.

Figures 1A, 1B:
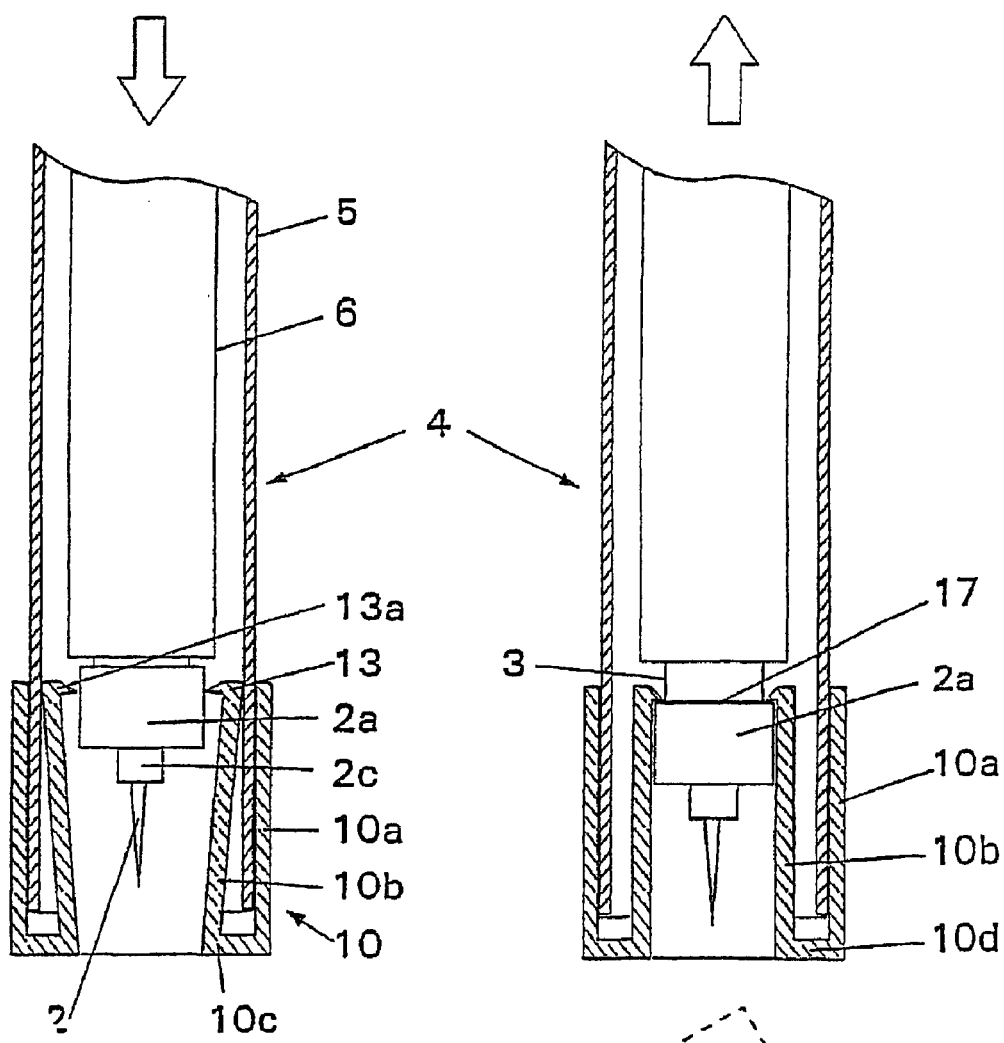
FIGS. 1a and 1b are vertical sections of an embodiment of the device, illustrating two steps in the process of extracting a hypodermic needle.

A hypodermic needle 2 forms one piece with a connecting end in the form of a hollow socket 2a whose inner face has a connector consisting of at least one rib 2b. This hollow socket 2a is preferably made of a material which is elastically deformable so that it can dilate elastically and allow the rib 2b to engage with a complementary connector, such as a rib, a groove or a thread 3a, located on the outer face of a tip 3 of an injection instrument 4. It will be observed that, as shown in FIG. 1, the semicircular profile of the rib 2b makes it possible to convert in both directions an axial pressure into a radial component capable of deforming the socket 2a elastically.

In the embodiment illustrated here this injection instrument 4 resembles a ball-point pen in that it has a cylindrical barrel 5 housing a cartridge 6 intended to contain a dose of medicinal substance to be injected, the forward end of which terminates in the connecting tip 3 intended to be pushed into the socket 2a of the hypodermic needle 2. This injection instrument 4 is of a known type, such as those disclosed e.g. in U.S. Pat. No. 5,092,842, in U.S. Pat. No. 5,114,406 or in EP 0 359 761, in which the hypodermic needle is retractable inside the cylindrical barrel in its rest position. Since this instrument does not form part of the present invention, the rest of its structure and operation will not be described in greater detail.

The device 10 for separating the connecting end 2a of the hypodermic needle 2 from the tip 3 of the injection instrument 4 shown in FIGS. 1a, 1b takes the form of a cylindrical receptacle consisting of two concentric walls, an exterior guiding wall 10a and an interior wall formed of a number of elastic arms 10b. The exterior wall 10a and the elastic arms 10b form one piece with a flat annular part 10c. The free ends of the elastic arms 10b terminate in locking elements 13 which extend towards the inner faces of these elastic arms 10b thereby defining an opening 17 of variable diameter. The rim of this opening 17 is delimited by bevelled faces 13a of the locking elements 13.

This bevelled face 13a has the effect that, when the used hypodermic needle 2 is brought against it, guided by the cylindrical surface 5 of the barrel of the injection instrument 4 sliding within the inner face of the exterior cylindrical surface 10a of the extraction device 10, which serves as a guiding surface for it, and when a downward axial pressure is exerted, the needle creates a centrifugal radial component which allows the elastic arms 10b to be parted as shown in FIG. 1a, increasing the diameter of the opening 17 until it allows the connecting end 2a of the hypodermic needle 2 to be inserted through the opening 17.

As is shown in FIG. 1b the elastic arms 10b resume their initial position as soon as the upper face of the connecting end 2a is below the level of the locking elements 13. If traction is then exerted on the injection instrument 4 while the extraction device 10 holding the hypodermic needle 2 is held the injection instrument 4 can be separated from the needle 2.

Figure 2:
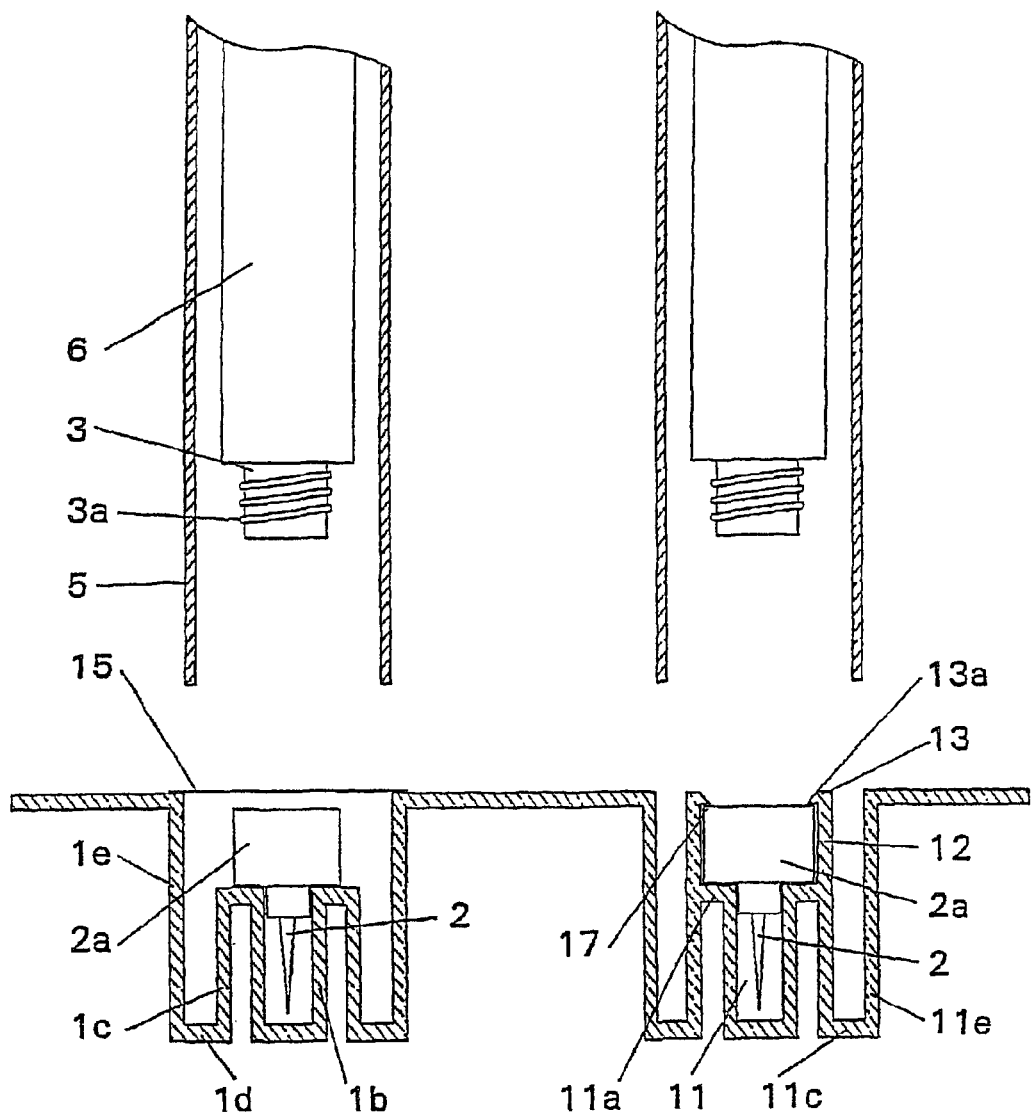
FIG. 2 is a vertical section of a first variation.

FIG. 2 shows a portion of an assembly which has, in addition to a variation 11–11e of the device for extracting the needle 2 in FIGS. 1a, 1b, a container 1–1e for storage of a sterile hypodermic needle 2.

This storage container 1–1e has a housing 1 delimited by a cylindrical wall 1b and intended to receive the hypodermic needle 2. The diameter of the cylindrical wall 1b of the housing 1 for the hypodermic needle 2 is calculated to permit adjustment of an intermediate portion 2c located between the socket 2a and the needle properly so-called 2, so that this needle 2 can be correctly positioned. The upper lip 1a of the cylindrical wall 1b acts as the stop to a length of travel [?] provided between the socket 2a and the intermediate portion 2c of the needle 2. A second cylindrical wall 1c, coaxial with the cylindrical wall 1b of the housing 1 for the needle 2, surrounds the latter up to the point where it reaches the same level as the base of the housing 1 delimited by the cylindrical wall 1b. A radial portion 1d of this wall extends outwards and terminates in a third cylindrical wall 1e, concentric with the other two walls but extending back to a higher level than they do and bounding an access opening 7.

The overall appearance of the extraction device 11–11e properly so called is similar to that of the container 1–1e intended to contain a sterile needle 2. It too has a housing 11 to receive a needle 2. This housing 11 is identical to the housing 1. Its upper end terminates in a lip 11a on which rests the outer face of the socket forming the connecting end 2a of the needle 2. In this extraction device the second cylindrical wall 11c surrounding the wall bounding the housing 11 is continued upwards as far as the level of the upper end of the exterior wall 11e by a number of elastic arms 12 which combine to form a cylindrical receptacle whose diameter matches that of the connecting end 2a of the hypodermic needle 2.

These elastic arms 12 which play the same role as the elastic arms 10b in FIGS. 1a, 1b also terminate in locking elements 13 pointing inwards into the receptacle formed between the elastic arms 12 and bound an opening 17 of variable diameter. The length of the elastic arms 12 is selected so that the lower or inner face of the locking elements 13 is located precisely at the level of the upper or outer face of the connecting end 2a of the needle 2 when the lower face of this end 2a rests on the lip 11a. The upper or outer face 13a of these locking elements is also bevelled and serves the same purpose as in the previous embodiment, and therefore reference may be made to the equivalent description of the way in which that embodiment functions.

The upper rim of the storage container 1–1e for a sterile needle 2 and the upper rim of the exterior wall 11e of the extraction device 11–11e are linked to each other by a horizontal wall 1f. This wall 1f can, preferably, link the container 1–1e and the extraction device 11–11e to other pairs of storage containers and extraction devices of the same type.

In this variation the needle, when separated from the injection instrument 4, remains trapped in the housing 11 and is therefore protected from any contact.

Figure 3C:
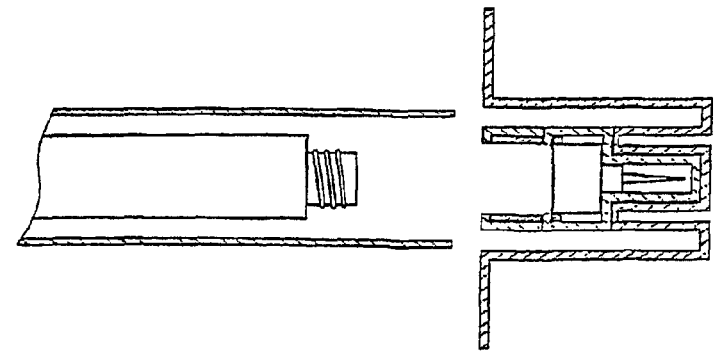
FIGS. 3a, 3b, 3c are vertical sections of a second variation, representing three successive steps in the use of a hypodermic needle.

In the variation described in connection with FIG. 2 two distinct containers 1–1e and 11–11e respectively are required for each needle 2, one for the sterile needle 2 and the other for the needle 2 after use. We shall now describe, in connection with FIGS. 3 through 3c, a variation in which a single container can successively receive a sterile needle 2 and then allow the extraction and storage of the needle 2 after use, thereby making it possible to double the capacity of a single stand of needles as compared with the preceding embodiment.

Figure 3B:
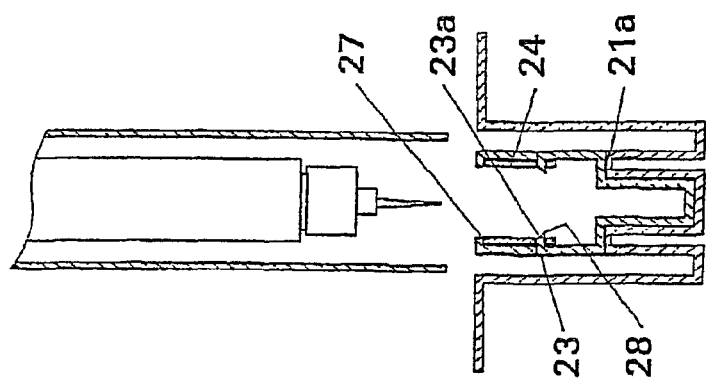

In this variation there is a container 21–21e, more or less similar to the preceding containers, with three concentric cylindrical walls 21b, 21c, 21e, but in which the housing 21 formed by the cylindrical wall 21b, instead of receiving the hypodermic needle 2 directly, receives another receptacle 22 composed of two coaxial cylindrical pieces, one below, 22a, accommodated and fixed within the wall 21b of the housing 21, the other above, 22b, extending as far as the upper end of the outer cylindrical face 21e of the container 21–21e and itself divided into two parts by an opening 28 formed by the locking elements 23 (FIG. 3b).

The upper part of the receptacle 22, positioned above the housing 21 of the needle 2 properly so called has approximately twice the height of the connecting end 2a of the hypodermic needle 2. Elastic arms 22c are located in the lower part of the upper cylindrical wall 22b of the receptacle 22. These elastic arms 22c are of similar design to that of the elastic arms 19 in FIG. 2. They too terminate at their upper ends in locking elements 23 which are identical to and play the same role as the locking elements 13 in the previous Figures.

Figure 3A:
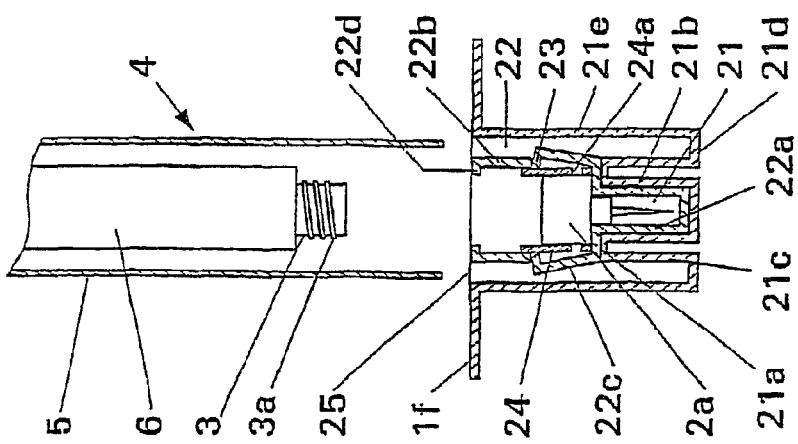

As FIG. 3a shows a ring 24, having at its base passages 24a, surrounds the connecting end 2a of the needle 2. The dimensions of this ring 24 are such that it projects slightly beyond the upper face of the connecting end 2a of the needle 2, so that the locking elements 23 and the elastic arms 22c are kept back, as is shown in FIG. 3a. The diameter of the ring 24 is selected so that the ring grips the connecting end 2a by friction. A cap 25 which can be pierced closes the upper opening of the container 21–21e.

The user wishing to connect the needle 2 enclosed in this container 21–21e to the tip 3 of the injection instrument 4 positions the lower rim of the cylindrical wall 5 of the barrel of this instrument 4 on the centre of the cap 25 and then exerts axial pressure on the instrument 4. The first effect of this pressure is the piercing of the cap 25. The instrument 4 is then guided by the cylindrical wall 21e of the container 21–21e, bringing the tip 3 of the instrument 4 into the cavity of the socket forming the connecting end 2a of the hypodermic needle 2. The connection between this needle 2 and the interior wall of the socket is effected by applying axial pressure to the instrument 4 sufficient to achieve deformation of a rib 2b located on the inner face of the socket 2a in order to allow it to be locked on to a groove or thread 3a located on the tip 3 of the injection instrument 4.

If the needle 2 connected to the tip 3 is withdrawn along its axis it draws with it the ring 24 until the latter rests against a lip 22d of an access opening 27 in the extraction device, this lip being formed at the upper end of the cylindrical wall 22b of the receptacle 22. The diameter of this access opening 27 is approximately the same as that of the connecting end 2a of the needle 2, and therefore allows the needle to freely enter into or withdraw from the container 21–21e, causing slippage between the connecting end 2a and the ring 24. It is obvious that the frictional force between these two pieces must be less than the axial tractional force which must be exerted between the needle 2 and the injection instrument 4 in order to separate the needle 2 from this instrument.

As is shown in FIG. 3b, at the end of the movement of the ring 24 the passages 24a are opposite the locking elements 23, allowing the latter to pass through them because of the elasticity of the arms 29c which resume their initial shape and to project from the inner face of the ring 24.

Once the sterile needle 2 has been removed from the container in the manner described the container is ready to receive the needle after use and to separate it from the injection instrument 4. The used needle 2 is inserted into the extraction device through the access opening 27 and then, as can be seen, the separation is effected in a manner identical to what has been described in connection with FIG. 2. The parts of the locking elements 23 which project within the ring 24 have oblique upper faces 23a, so that the axial pressure exerted on these oblique faces when the connecting end 2a of the needle 2 is inserted forces them apart, allowing the connecting end to be pushed until it rests against the lip 21a formed at the upper end of the housing 21 of the needle 2.

The locking elements 23 are now freed and can therefore close again above the upper face of the connecting end 2a of the needle 2, trapping the latter in the container 21–21e. The injection instrument 4 can then be separated by applying traction along its axis and by holding the container 21–21e whose ergonomic shape constitutes an interface making it easy to grasp, whereas this operation would very difficult or even impossible for an inexperienced user if the container were not there. The advantage of the ergonomic interface is still further increased when several containers are arranged side by side and linked by a shared horizontal wall 1f, which improves the purchase on the shared stand supporting these containers 21–21e.

Figure 4A:
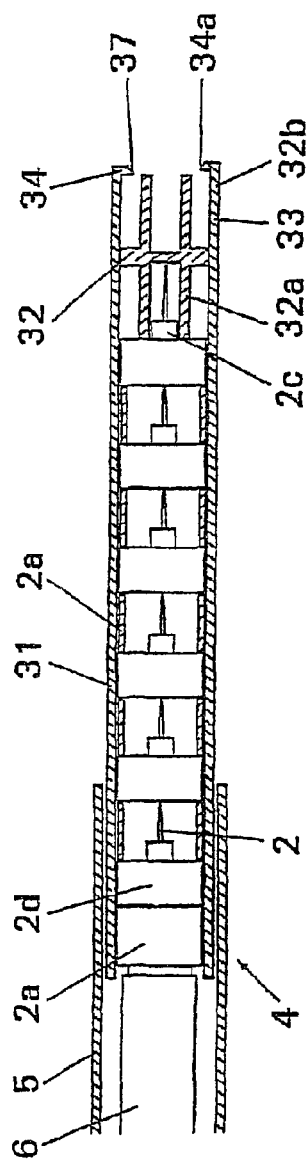
FIGS. 4a, 4b, 4c are sections of a third variation, representing three successive steps in the use of a hypodermic needle.
Figure 4B:
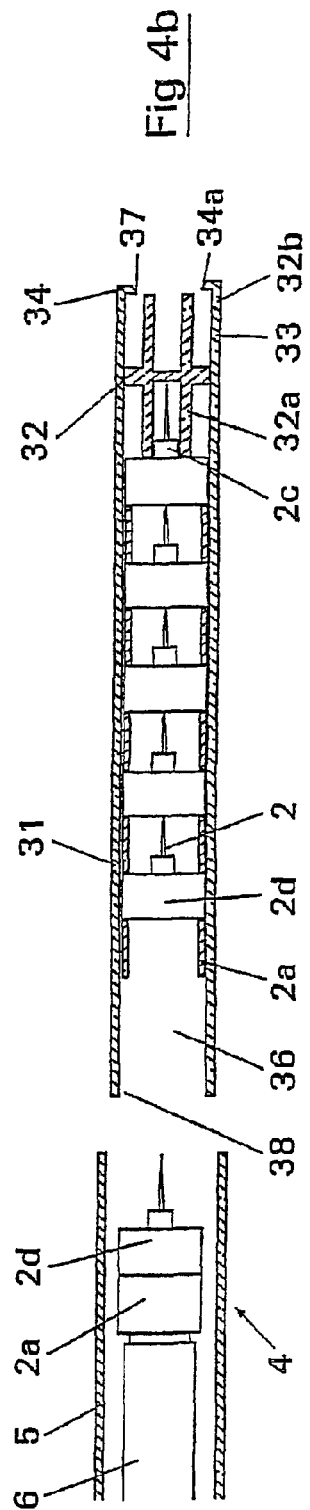
Figure 4C:
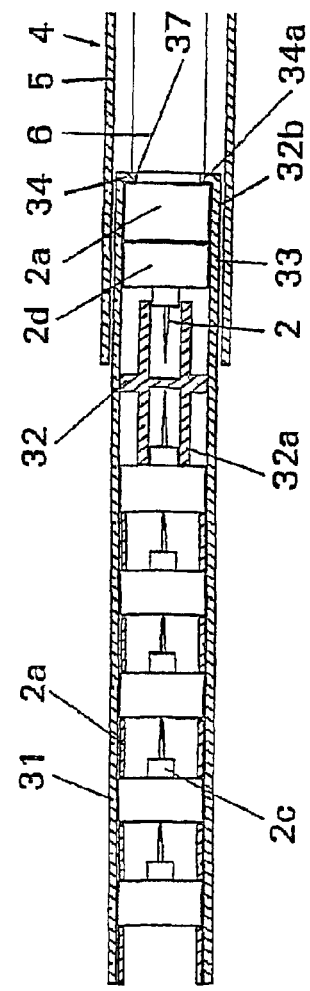

In the variation illustrated in FIGS. 4a through 4c the container takes the form of a tubular body 31 bounding a cylindrical housing 36 accessed by an opening 38. The hypodermic needles are inserted successively into the housing 36. In this variation the connecting socket 2a of the needle 2 also serves as a spacer which makes it possible to keep the needles 2 separated from one another along their axis. Since this connecting socket 2a has to dilate radially when it is being connected to the tip 3 of the injection instrument 4 the external diameter of this connecting socket 2a is very slightly less than the internal diameter of the tubular body 31, in order to prevent the connection operation from causing the needle to jam in the tubular body 31, thus making it difficult to remove. The needles 2 are held within the tubular body 31 by another portion 2d located between the connecting socket 2a and the needle 2 whose diameter matches the internal diameter of the tubular body 31.

These needles 2 are accessible from one end of the tubular body 31 and the connection with the tip 3 of the injection instrument is effected in the manner described above. In this example the number of needles 2 accommodated in the tubular body is six. The first needle 2, which will be used last, is held in position by a support 32 which is positioned to slide in the tubular body 31. The frictional force between this support 32 and the interior wall of the tubular body 31 is however selected so as to resist the pressure required to effect the connection between the needle 2 and the injection instrument 4. This support 32 has two axial housings 32a, 32b placed in mirror symmetry in relation to the centre of the support 32 and with their outward-facing ends open. The diameter of these housings is selected to receive the intermediate portion 2c of the hypodermic needle 2.

This support 32 and the axial housings 32a, 32b make it possible for the needles 2 withdrawn from the tubular body 31 to be inserted, after use, into the other end of the same tubular body 31 and then separated from the injection instrument 4. For this purpose the other end has elastic arms 33 terminating in locking elements 34 like those in the embodiments previously described. These locking elements 34 have bevelled outer faces 34a bounding an opening of variable diameter. The bevelled faces 34a are intended to convert the axial force exerted on them by the portion 2d of the needle 2 into a radial component making it possible for the elastic arms 33 to bend and thus increase the diameter of the opening 37 to allow the connecting end 2a to pass through it. The support 32 must therefore slide each time that a used needle 2 is inserted through the end of the tubular body 31 provided with locking elements 34.

As is shown in FIG. 4c these locking elements 34 engage in a space located between the end of the connecting socket 2a and the cartridge 6, so that traction exerted between the injection instrument 4 and the tubular body 31 makes it possible to separate the instrument 4 from the needle 2 which is trapped in the tubular body 31. The ergonomic shape of the latter allows a good grip and thus facilitates the performance of the operation.

What is claimed is:

1. Device for separating a connecting end of a hypodermic needle from a tip of an injection instrument, the connecting end of the hypodermic needle having connectors complementary to connectors on the tip, one of the connectors having radial elasticity and devices for converting an axial force exerted between the needle and the injection instrument into at least one radial component capable of deforming the connectors, comprising an opening delimited by locking elements forming one piece with elastic pieces to allow its diameter to vary between a minimum diameter and a maximum diameter at least equal to the diameter of the connecting end and at least one piece associated with the locking elements for the purpose of converting an axial force exerted on the one piece with elastic pieces into at least one radial component capable of being applied to the elastic pieces to deform them radially so as to increase the diameter of the opening when the connecting end is displaced along its axis with its needle pointing forward through the opening and to restore its initial diameter after the connecting end has passed through it and allow the locking elements to engage with the rear face of the connecting end, wherein the device has a guiding surface concentric with the opening, wherein the device has a cylindrical housing divided longitudinally into two parts whose respective lengths are approximately equal, matching the length of the connecting end, by the opening delimited by the locking elements which form one piece with elastic arms attached to one end of the cylindrical housing which communicates with the exterior at its other end through an access opening having a diameter approximately equal to that of the connecting end of the hypodermic needle, a ring, having an internal diameter approximately equal to that of the access opening, positioned to slide in the cylindrical housing, being capable of occupying two limiting positions within the housing, in one of which positions it is adjacent to the access opening, the ring having passages in such an arrangement and of such dimensions as to allow the locking elements to project on the inner face of this ring when the latter is adjacent to the access opening, while in its other limiting position it holds the locking elements forming one piece with the elastic arms back from the connecting end to which it adheres by friction.

2. Device according to claim 1, wherein the said opening serves as the access opening in a closed housing.

3. Device according to claim 1, wherein one rim of the said guiding surface is linked by a horizontal surface to a storage container for a hypodermic needle.

4. Device according to claim 1, wherein it has the form of a tubular body in which a number of hypodermic needles are successively placed in corresponding positions so as to be accessible to the injection instrument from one end of the tubular body, while the other end has the radially elastic locking elements to allow its diameter to vary between a minimum diameter and a maximum diameter at least equal to that of the connecting end and at least one piece associated with the locking elements for the purpose of converting an axial force exerted on the piece into at least one radial component capable of being applied to the locking elements so as to deform them radially in order to increase the diameter of the opening.

* * * * *